United States Patent
Barua

(10) Patent No.: US 12,028,103 B1
(45) Date of Patent: *Jul. 2, 2024

(54) PHYSIOLOGICAL SIGNAL ACQUISITION SYSTEM AND METHOD WITH IMPROVED NOISE AND COMMON MODE REJECTION PERFORMANCE AND SIGNAL QUALITY

(71) Applicant: NeuroWave Systems Inc., Cleveland, OH (US)

(72) Inventor: Sankar Barua, Stow, OH (US)

(73) Assignee: NeuroWave Systems Inc., Cleveland, OH (US)

( * ) Notice: Subject to any disclaimer, the term of this patent is extended or adjusted under 35 U.S.C. 154(b) by 51 days.

This patent is subject to a terminal disclaimer.

(21) Appl. No.: 17/879,253

(22) Filed: Aug. 2, 2022

Related U.S. Application Data

(63) Continuation of application No. 14/986,006, filed on Dec. 31, 2015, now Pat. No. 11,444,646.

(51) Int. Cl.
*H04B 1/16* (2006.01)
*A61B 5/291* (2021.01)
*A61B 5/316* (2021.01)

(52) U.S. Cl.
CPC ........... *H04B 1/1638* (2013.01); *A61B 5/291* (2021.01); *A61B 5/316* (2021.01); *A61B 2562/222* (2013.01)

(58) Field of Classification Search
None
See application file for complete search history.

(56) References Cited

U.S. PATENT DOCUMENTS

| | | | |
|---|---|---|---|
| 6,208,888 B1* | 3/2001 | Yonce | A61B 5/305 600/509 |
| 2012/0088984 A1* | 4/2012 | Al-Ali | A61B 5/369 600/383 |
| 2013/0328627 A1* | 12/2013 | Krohn | A61B 5/6801 330/149 |

* cited by examiner

*Primary Examiner* — Jay B Shah
(74) *Attorney, Agent, or Firm* — Brian Kolkowski

(57) ABSTRACT

The present invention relates to the acquisition, processing, and monitoring of signals, and particularly to the acquisition, processing, and monitoring of electrophysiological signals. More particularly, the present invention relates to the acquisition, processing, and monitoring electroencephalography (EEG) signals representing cortical/brain activity. Further, the present invention relates to a method and apparatus for acquiring such signals in the presence of electrical interference and noise. More particularly, the present invention relates to systems and methods for filtering out and rejecting electrical interference and noise while maintaining or improving the quality of the underlying physiological signal and preventing perturbation or introduction of artifacts into the physiological signal.

10 Claims, 10 Drawing Sheets

PHYSIOLOGICAL SIGNAL ACQUISITION SYSTEM AND METHOD WITH IMPROVED NOISE AND COMMON MODE REJECTION PERFORMANCE AND SIGNAL QUALITY

CROSS-REFERENCE TO RELATED APPLICATIONS

This application is a continuation of U.S. patent application Ser. No. 14/986,006, which was filed on Dec. 31, 2015. The specification and drawings of the above application is hereby incorporated by reference in its entirety.

LICENSE RIGHTS—FEDERALLY SPONSORED RESEARCH

The U.S. Government has a paid-up license in this invention and the right in limited circumstances to require the patent owner to license others on reasonable terms provided for by the terms of contract number W81WH-11-C-0078 awarded by United States Army Medical Research Acquisition Activity (USAMRAA).

BACKGROUND OF THE INVENTION

1. Field of the Invention

The present invention relates to the acquisition, processing, and monitoring of signals, and particularly to the acquisition, processing, and monitoring of electrophysiological signals. More particularly, the present invention relates to the acquisition, processing, and monitoring electroencephalography (EEG) signals representing cortical/brain activity. Further, the present invention relates to a method and apparatus for acquiring such signals in the presence of electrical interference and noise. More particularly, the present invention relates to systems and methods for filtering out and rejecting electrical interference and noise while maintaining or improving the quality of the underlying physiological signal and preventing perturbation or introduction of artifacts into the physiological signal.

2. Technology Review

Physiological signals are very low in amplitude and in frequency contents in general. A typical EEG signal acquired from frontal lobes is 50 μV in amplitude and can be as low as 10 μV during cortical suppression. Compared to ECG signal, which is typically a few millivolts, EEG signal is 10-20 folds smaller. To provide a different perspective, a typical low noise instrumentation amplifier (in-amp), which is inevitably used for physiological signal acquisition as it provides comparative advantage to differential signal over common mode signal by the factor of gain, can generate as much as a few microvolts of input referred noise. Therefore, to acquire such a noise-like-low-electrophysiological signal is a challenge and requires careful design considerations. The first challenge is noise, which must not submerge desired physiological signals, generated from the components used in analog front end. In other words, analog front end must reject noise to extent where signal-to-noise ratio qualifies high quality physiological signal acquisition. One design technique that is universally used to reduce noise is a low-pass filter in the front of in-amp. Physiological signals, and especially EEG signals, are typically comprised of very low frequencies (e.g., EEG signals are typically between 0.5 Hz to about 70 Hz, but can expand to between 0.125 Hz to about 120 Hz) compared to other signals or to the various artifacts, noise and interference. The low bandwidth feature becomes beneficial for physiological signal acquisition system and makes low-pass filter able to control noise, which is typically specified for EEG acquisition system not to be more than 20/pp. Therefore, a low-pass filter having low cutoff frequency in the physiological signal acquisition analog front end is essential. The necessity becomes inevitable as it must also act as anti-aliasing filter when cost and space saving integrated solution, in-amp and analog to digital converter in one package with no anti-aliasing filter, such as TI ADS1299 is used.

The analog front end, consisting of low-pass filter and in-amp, is able to acquire noise-like-low-electrophysiological signal as long as the environment it is used is ideal, meaning no external interference such as RFI, EMI, or power frequency interference exists. The RFI and EMI are high frequency interference in nature and low-pass filter is able to reject most of them in general. However, the power frequency interference, which is 50/60 Hz signal coming from AC Mains, remains within the physiological signal band of interest and passes through. FIG. 5. shows how 50/60 Hz power signal is coupled to a floating patient. 50/60 Hz power signal can also be coupled to the analog front end by different means such as cable, PCB traces and so forth. Considering a typical 20 pf iso-barrier, as high as a few volts of 50/60 Hz common mode signal can couple to floating patient and result in 100s of micro-volts of interference in the acquired signal. Such interference completely submerges physiological signals and makes the analog front end with traditional filter impractical for high quality physiological signal acquisition.

50/60 Hz interference is a common mode signal and appears to in-amp of analog front end. In general ins-amp itself achieves common mode rejection ratio (CMRR) as high as 100 or 110 dB and hence able to reject most of the interference as long as interference remains common mode signal at its inputs. However, in practice, some of the common mode signal is converted to differential signal as it travels through mismatched impedances. Impedance mismatch or imbalance mainly results in from the lack of identical low-pass filters and disparate patient electrode impedances. Patient electrode impedance inherently varies from 500 ohms to 10s of kilo ohms. The wider is the difference; the worst is the common mode rejection. Device manufacturers usually put accepted limit on electrode impedance difference in order to control CMRR. To match low-pass filters, traditionally 1% or less tolerance resistors and 2% tolerance capacitors are used. However, even using the state of the art component matching technology shown in FIG. 2, achieving a system level CMRR of 80-90 dB is barely possible, where 110 dB or more of system level CMRR is essential to acquire noise-like-low-electrophysiological signals. Patient protection circuits, electrode lead wires, and any other component used in analog front end make the situation even worse.

It should therefore be appreciated that there is the need for an analog front end that, when used for electrophysiological signal acquisition, provides a high input impedance required to achieve high system level CMRR while at the same time providing adequate filtering of unwanted noise and interference from stop-band so that quality physiological acquisition system can be attained. The present invention fulfills this need.

It is therefore an object of the present invention to provide a system for acquiring physiological signals in the presence of noise and interference that is capable of removing as much of such noise, interference, and common mode signal possible. It is a further object of the invention to minimize noise on the front end so that there is less noise to remove. It is still further an object of the present invention to simultaneously increase input impedance of electrical leads in order to ensure a high common mode rejection ratio while simultaneously avoiding perturbation of the physiological signal and causing of additional artifacts and signal quality issues.

SUMMARY OF THE INVENTION

The present invention relates to the acquisition, processing, and monitoring of signals, and particularly to the acquisition, processing, and monitoring of electrophysiological signals. More particularly, the present invention relates to the acquisition, processing, and monitoring electroencephalography (EEG) signals representing cortical/brain activity. Further, the present invention relates to a method and apparatus for acquiring such signals in the presence of electrical interference and noise. More particularly, the present invention relates to systems and methods for filtering out and rejecting electrical interference and noise while maintaining or improving the quality of the underlying physiological signal and preventing perturbation or introduction of artifacts into the physiological signal.

Preferably, this system is used for the brain wave or activity monitoring of a single patient or multiple patients. Preferably, the system is a multi-electrode EEG system; however, depending on purpose of use and cost, systems may have as few as 3 electrodes: with at least 2 electrodes for measurement of brain or cortical activity, one for each hemisphere of the subject's rain, and at least one reference electrode. Preferably, the system or monitor of the present invention also includes one or more methods or algorithms for detecting or quantifying brain or cortical activity, and/or level of consciousness, seizure detection, level of sedation and the like. Preferably, the system or monitor can also measure muscle activity, EMG and EOG, contained in the EEG signal, as well as other spectral components of the EEG signal. These components may include but are not limited to the suppression ratio which is the ratio of time where there is no substantial brain or cortical activity to the time where there is cortical or brain activity shown in the EEG signal and burst count which is the number of high frequency bursts. In addition, the system and related methods can use other sensors that measure physiological signals which directly or indirectly result in or from brain dysfunction, or effect or result from brain activity.

Preferably, the system should operate in real time. One example of real-time operation is the ability of the system to acquire, process and analyze physiological signals substantially instantaneously, rather than being limited to analysis that takes place minutes or hours afterward.

The present invention comprises hardware and software components designed to acquire physiological signals and provide robust front-end pre-processing to provide a high quality physiological signal for analysis. The system comprises circuitry utilizing filter(s) that aims to remove many forms of interference from the physiological signal and provide only the relevant physiological signal to the system for processing and analysis. The filtering elements of this circuitry are different from those typically used in such applications and help to more accurately and effectively reject undesired portions of the signal such as common mode signal, artifacts, noise and other interference while also minimizing perturbation of the desired physiological signal. The system has a much higher signal to noise ratio due to this circuitry than typical physiological signal. These improvements in the circuitry and filtering allow for greater efficiency and utility of the system and methods of using it.

The physiological signal filtering of the present invention provides several other advantages the increase the utility and efficacy of physiological monitoring systems and methods. For example, the circuitry and methods of using said circuitry described herein allow for the use of longer sensor or electrode leads than traditional systems without loss of signal integrity through weakening signal or increases in noise or other interference. Longer leads allow more versatility in use of the system for different environments or arrangements of equipment within the monitoring area. Preferably, the circuitry of the present invention allows for leads that are at least 25% longer than traditional leads without loss of signal integrity. More preferably, the circuitry allows for at least 35% longer leads without loss of signal integrity. Still more preferably, the circuitry allows for at least 40% longer leads without loss of signal integrity. Yet more preferably, the circuitry allows for at least 50% longer leads without loss of signal integrity. Even more preferably, the circuitry allows for at least 60% longer leads without loss of signal integrity. Still yet more preferably, the circuitry allows for at least 65% longer leads without loss of signal integrity. Even still preferably, the circuitry allows for at least 75% longer leads without loss of signal integrity.

Another advantage that the circuitry and methods of using of the present invention is an increase in the common mode rejection ratio (CMRR) which is the ratio of rejection of undesired input signals (e.g., noise, artifacts, interference) common to all the input leads to the desired signal (i.e., the physiological signal being acquired). The higher the CMRR, then, means that more undesired signal is being rejected and very little of the desired signal is being rejected, or filtered out. Conventional physiological signal acquisition systems can typically exhibit CMRR values up to about 80 dB. However, the improved circuitry and methods of the present invention allow for significantly higher CMRR values, which represent a significant increase in the ability to reject unwanted signals and keep desired physiological signals. Preferably, the system has a common mode rejection ratio (CMRR) of at least 75 dB. More preferably, the system has a CMRR of at least 80 dB. Yet more preferably, the system has a CMRR of at least 85 dB. Still more preferably, the system has a CMRR of at least 90 dB. Even more preferably, the system has a CMRR of at least 95 dB. Still yet more preferably, the system has a CMRR of at least 100 dB. Yet still more preferably, the system has a CMRR of at least 105 dB. Even still more preferably, the system has a CMRR of at least 110 dB.

The processor or computer, and the methods of the present invention preferably contain software or embedded algorithms or steps that automatically identify artifacts and even more preferably remove the artifacts from the physiological signal, and automatically quantify brain or cortical activity, level of consciousness, identify seizures or other brain dysfunction, level of sedation based on the essentially artifact free EEG signal.

The system described in this invention also preferably incorporates a number of unique features that improve safety, performance, durability, and reliability. The system should be cardiac defibrillator proof, meaning that its electrical components are capable of withstanding the surge of electrical current associated with the application of a cardiac defibrillator shock to a patient being monitored by the system, and that the system remains operable after sustaining such a surge. The system should have shielded leads so as to reduce as much as possible the effects of external electromagnetic interference on the collection of biopotential or physiological signals from the patient being monitored by the system. The system should be auto-calibrating, more preferably capable of compensating for the potential differences in the gains of the input electrodes to the patient module. The system should be capable of performing a continuous impedance check on its electrode leads to ensure the suitability of monitored signals.

One embodiment of the present invention includes an analog front-end receiving differential-mode input signal from differential lines and outputting a signal relative to ground either in analog or digital form for physiological signal acquisition comprising: an instrumentation amplifier having gain setting option using external resistor, a first differential input terminal, a second differential input terminal, and an output signal terminal providing analog or digital output reference to ground, and a first gain resistor and a second gain resistor coupled in series providing a common-mode node; the open terminal of the first gain resistor and the open terminal of the second gain resistor being connected between the gain setting terminals of the instrumentation amplifier to set the gain, and a first unity-gain buffer having an input terminal and an output terminal, the input terminal being connected to the common mode node, and a bootstrapped low-pass filter comprising a first filter resistor, a first filter capacitor, a second filter resistor, and a second filter capacitor; the first capacitor and second capacitor coupled in series being connected between the first resistor and the ground terminal; the second resistor being connected between the first and second capacitor's junction node and the output terminal of the buffer so that the first capacitor can be bootstrapped with the same common mode voltage across it; the junction point between first resistor and the first capacitor, which is the output terminal of the bootstrap filter, being connected to the first differential input terminal of the instrument amplifier; the other terminal of the first resistor, which is the input terminal of the bootstrap filter, being connected to physiological input signal, and a second bootstrapped low-pass filter having an input terminal and an output terminal as defined in the first bootstrap filter; the output terminal of the second bootstrap filter being connected to the second differential input terminal of the instrument amplifier, and the input terminal of the second bootstrap filter being connected to physiological input signal, and a second unity-gain buffer having an input terminal and an output terminal, the input terminal being connected to the same common mode node and the output terminal being connected to the second bootstrap filter in the same manner as connected in the first bootstrap filter.

Another embodiment of the present invention includes an analog front-end receiving differential-mode input signal from differential lines and outputting a signal relative to ground either in analog or digital form for physiological signal acquisition comprising: an instrumentation amplifier having a first differential input terminal, a second differential input terminal, and an output signal terminal providing analog or digital output reference to ground, and a first unity-gain buffer having an input terminal and an output terminal, the input terminal being connected to the first differential input terminal of the instrumentation amplifier, and a bootstrapped low-pass filter comprising a first filter resistor, a first filter capacitor, a second filter resistor, and a second filter capacitor; the first capacitor and second capacitor coupled in series being connected between the first resistor and the ground terminal; the second resistor being connected between the first and second capacitor's junction node and the output terminal of the buffer so that the first capacitor can be bootstrapped with the same voltage across it; the junction point between first resistor and the first capacitor, which is the output terminal of the bootstrap filter, being connected to the first differential input terminal of the instrument amplifier; the other terminal of the first resistor, which is the input terminal of the bootstrap filter, being connected to physiological input signal, and a second bootstrapped low-pass filter having an input terminal and an output terminal as defined in the first bootstrap filter; the output terminal of the second bootstrap filter being connected to the second differential input terminal of the instrument amplifier, and the input terminal of the second bootstrap filter being connected to physiological input signal, and a second unity-gain buffer having an input terminal and an output terminal, the input terminal being connected to the second differential input terminal of the instrumentation amplifier and the output terminal being connected to the second bootstrap filter in the same manner as connected in the first bootstrap filter.

Yet another embodiment of the present invention includes an analog front-end receiving differential-mode input signal from differential lines and outputting a signal relative to ground either in analog or digital form for physiological signal acquisition comprising: an analog front-end as described above, and a third bootstrap filter; the output terminal of the third bootstrap filter being connected to the input terminal of the first bootstrap filter and the input terminal of the third bootstrap filter being connected to the physiological input signal; the junction node of the first filter capacitor and the second filter capacitor of the first bootstrap filter being connected to the open terminal of the second resistor of the third bootstrap filter, and a forth bootstrap filter; the output terminal of the forth bootstrap filter being connected to the input terminal of the second bootstrap filter and the input terminal of the forth bootstrap filter being connected to the physiological input signal; the junction node of the first filter capacitor and the second filter capacitor of the second bootstrap filter being connected to the open terminal of the second resistor of the forth bootstrap filter.

Still another embodiment of the present invention includes an analog front-end receiving differential-mode input signal from differential lines and outputting a signal relative to ground either in analog or digital form for physiological signal acquisition comprising: an analog front-end as described above, and a third bootstrap filter; the output terminal of the third bootstrap filter being connected to the input terminal of the first bootstrap filter and the input terminal of the third bootstrap filter being connected to the physiological input signal; the junction node of the first filter capacitor and the second filter capacitor of the first bootstrap filter being connected to the open terminal of the second resistor of the third bootstrap filter, and a forth bootstrap filter; the output terminal of the forth bootstrap filter being connected to the input terminal of the second bootstrap filter and the input terminal of the forth bootstrap filter being connected to the physiological input signal; the junction node of the first filter capacitor and the second filter capacitor of the second bootstrap filter being connected to the open terminal of the second resistor of the forth bootstrap filter.

Yet another embodiment of the present invention includes an analog front-end receiving differential-mode input signal from differential lines and outputting a signal relative to ground either in analog or digital form for physiological signal acquisition comprising: an analog front-end as described above, and a third unity-gain buffer having an input terminal and an output terminal, the output terminal of which being connected to the input terminal of the first bootstrap filter, and a third bootstrap filter; the output terminal of the third bootstrap filter being connected to the input terminal of the third unity-gain buffer and the input terminal of the third bootstrap filter being connected to the physiological input signal; the open terminal of the second resistor of the third bootstrap filter being connected to the output terminal of the third buffer, and a forth unity-gain buffer having an input terminal and an output terminal, the output terminal of which being connected to the input terminal of the third bootstrap filter, and a forth bootstrap filter; the output terminal of the forth bootstrap filter being connected to the input terminal of the forth unity-gain buffer and the input terminal of the third bootstrap filter being connected to the physiological input signal; the open terminal of the second resistor of the forth bootstrap filter being connected to the output terminal of the forth buffer.

Still another embodiment of the present invention includes an analog front-end receiving differential-mode input signal from differential lines and outputting a signal relative to ground either in analog or digital form for physiological signal acquisition comprising: an analog front-end as described above, and a third unity-gain buffer having an input terminal and an output terminal, the output terminal of which being connected to the input terminal of the first bootstrap filter, and a third bootstrap filter; the output terminal of the third bootstrap filter being connected to the input terminal of the third unity-gain buffer and the input terminal of the third bootstrap filter being connected to the physiological input signal; the open terminal of the second resistor of the third bootstrap filter being connected to the output terminal of the third buffer, and a forth unity-gain buffer having an input terminal and an output terminal, the output terminal of which being connected to the input terminal of the third bootstrap filter, and a forth bootstrap filter; the output terminal of the forth bootstrap filter being connected to the input terminal of the forth unity-gain buffer and the input terminal of the third bootstrap filter being connected to the physiological input signal; the open terminal of the second resistor of the forth bootstrap filter being connected to the output terminal of the forth buffer.

Yet another embodiment of the present invention includes an analog front-end receiving differential-mode input signal from differential lines and outputting a signal relative to ground either in analog or digital form for physiological signal acquisition comprising: an instrumentation amplifier having gain setting option using external resistor, a first differential input terminal, a second differential input terminal, and an output signal terminal providing analog or digital output reference to ground, and a first gain resistor and a second gain resistor coupled in series providing a common-mode node; the open terminal of the first gain resistor and the open terminal of the second gain resistor being connected between the gain setting terminals of the instrumentation amplifier to set the gain, and an unity-gain buffer having an input terminal and an output terminal, the input terminal being connected to the common mode node, and a differential bootstrapped low-pass filter comprising a first filter resistor, a first filter capacitor, a second filter resistor, and a second filter capacitor; the first capacitor and second capacitor coupled in series being connected between the first resistor and the second resistor; the open terminal of the first resistor and the open terminal of the second resistor being connected to physiological signal; the junction point of the first resistor and the first capacitor being connected to the first differential terminal of the instrumentation amplifier; the junction point of the second resistor and the second capacitor being connected to the second differential terminal of the instrumentation amplifier, and a third filter capacitor connected between the junction point of the first capacitor and the second capacitor and the ground, and a third filter resistor connected to the third capacitor forming a low-pass filter; the open terminal of the third resistor being connected to the output terminal of the unity-gain buffer so that the first capacitor and the second capacitor are driven with the same common-mode voltage.

Still another embodiment of the present invention includes a system for physiological signal acquisition comprising: at least one bootstrapped filter comprising a resistor, a first capacitor and a second capacitor, and a unity gain buffer, the resistor and first capacitor forming a low-pass filter and the second capacitor is driven to have substantially the same upper and lower alternating current (AC) voltage; at least one instrumentation amplifier comprising at least two amplifiers; wherein the bootstrapped filter is connected to a common node of the at least two amplifiers external to the instrumentation amplifier and is adapted to remove common mode signal from the physiological signal prior to the signal entering the instrumentation amplifier.

Yet another embodiment of the present invention includes a system for physiological signal acquisition comprising: at least two bootstrapped filters each comprising a resistor, a first capacitor and a second capacitor, and a unity gain buffer, the resistor and first capacitor of each bootstrapped filter forming a low-pass filter and the second capacitor is driven to have substantially the same upper and lower alternating current (AC) voltage; at least one instrumentation amplifier comprising at least two amplifiers; wherein the bootstrapped filters are connected to a common node of the at least two amplifiers external to the instrumentation amplifier and are adapted to remove common mode signal from the physiological signal prior to the signal entering the instrumentation amplifier, and the system is adapted to allow additional channels to be added by adding an additional bootstrapped filter and using an existing channel as a reference.

Still another embodiment of the present invention includes a system for physiological signal acquisition comprising: at least two bootstrapped filters each comprising a resistor, a first capacitor and a second capacitor, and a unity gain buffer, the resistor and first capacitor of each bootstrapped filter forming a low-pass filter and the second capacitor is driven to have substantially the same upper and lower alternating current (AC) voltage; at least one instrumentation amplifier comprising at least three amplifiers; wherein one bootstrapped filter is connected to one of the at least three amplifiers of the instrumentation amplifier and another bootstrapped filter is connected to another of the at least three amplifiers of the instrumentation amplifier, and the bootstrapped filters are adapted to remove common mode signal from the physiological signal prior to the signal entering the instrumentation amplifier.

Yet another embodiment of the present invention includes a system for physiological signal acquisition comprising: at least one sensor having a lead; acquisition circuitry comprising a resistor, a first capacitor and a second capacitor; and a processor; wherein the at least one resistor and at least one first capacitor form a low-pass filter, the second capacitor has, or is driven to have, substantially the same upper and lower end AC voltage.

Still another embodiment of the present invention includes a method of acquiring physiological signals comprising steps of: providing a physiological signal acquisition system comprising at least one sensor having a lead and acquisition circuitry comprising at least one resistor, at least one first capacitor and at least one second capacitor, the at least one resistor and at least one first capacitor forming a low-pass filter; acquiring a physiological signal from a subject with the at least one sensor having a lead; transmitting the physiological signal from the sensor to the acquisition circuitry; driving the at least one second capacitor to have substantially the same upper and lower end AC voltage; and filtering the physiological signal with the acquisition circuitry.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. It is understood that many other embodiments of the invention are not directly set forth in this application but are none the less understood to be incorporated by this application. The accompanying drawings are included to provide a further understanding of the invention, and are incorporated in and constitute a part of this specification. The drawings illustrate various embodiments of the invention and together with the description serve to explain the principles and operation of the many embodiments of this invention.

DETAILED DESCRIPTION OF THE DRAWINGS AND PREFERRED EMBODIMENTS

Figure 1:
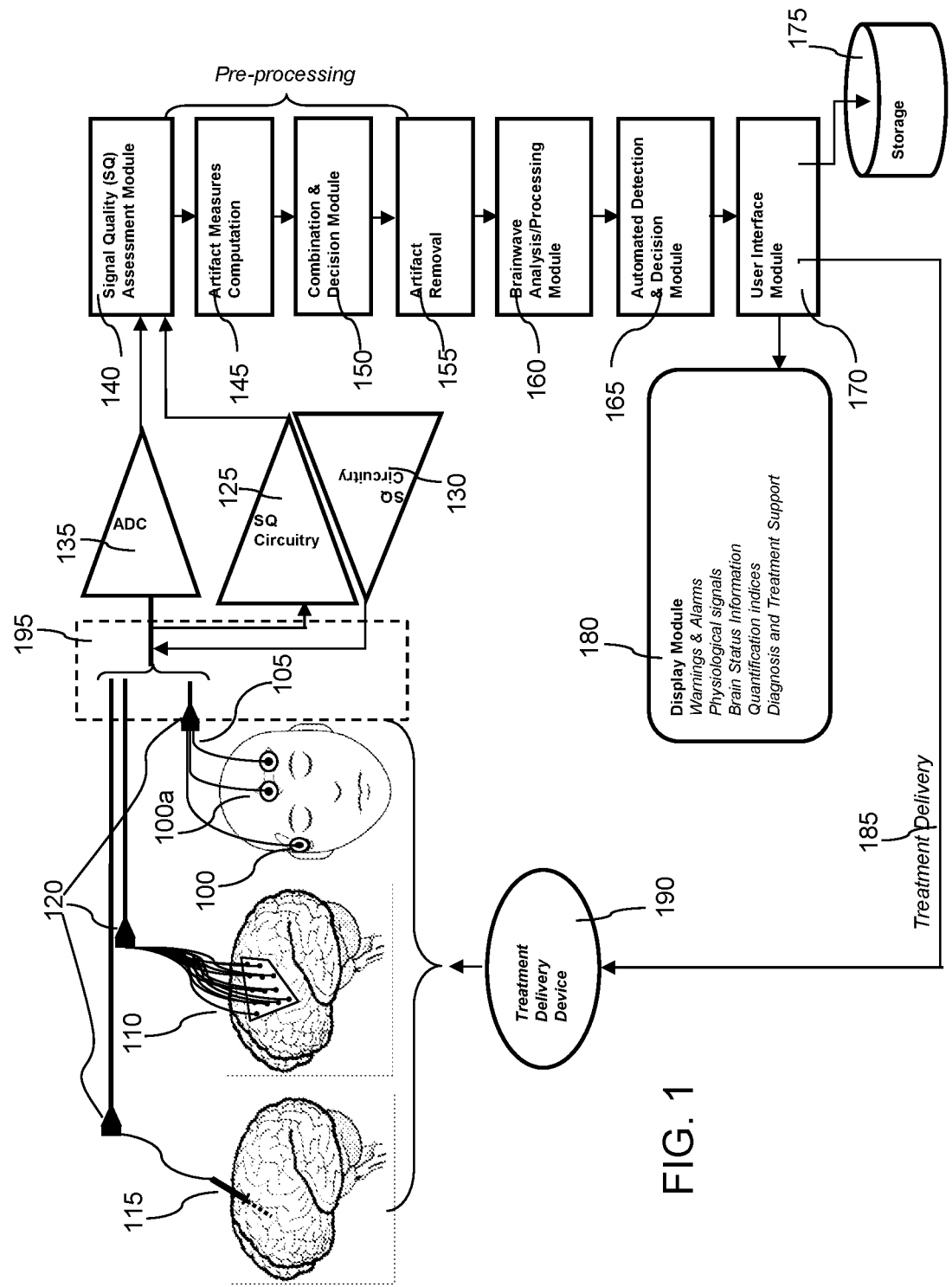
FIG. 1. Block diagram depicting a physiological signal (EEG) acquisition system utilizing the filtering and pre-processing system and methods of the present invention to monitor a subject's EEG and provide treatment for abnormal brain activity.

The present invention relates to the acquisition, processing, and monitoring of signals, and particularly to the acquisition, processing, and monitoring of electrophysiological signals. More particularly, the present invention relates to the acquisition, processing, and monitoring electroencephalography (EEG) signals representing cortical/brain activity. Further, the present invention relates to a method and apparatus for acquiring such signals in the presence of electrical interference and noise. More particularly, the present invention relates to systems and methods for filtering out and rejecting electrical interference and noise while maintaining or improving the quality of the underlying physiological signal and preventing perturbation or introduction of artifacts into the physiological signal.

For the present invention the subject whose EEG signal is being measured can be any type of animal, preferably a mammal, most preferably a human. Also, caregiver is understood to include not only those skilled in the use of EEG equipment and methodologies, such as doctors, physicians, anesthesiologists, EEG technologists, emergency response personnel, nurses, and the like, but also home care individuals, such as family members or other non-medically trained persons who may be responsible for caring for individuals in need of such equipment at home with minimal additional training.

Device or system embodiments of the present invention may include one or more of the following elements or components: sensors to acquire physiological signals from a subject, physiological signal acquisition circuitry for pre-processing the acquired physiological signals, a processor, and a display and/or other additional device for output of the physiological signal and/or data pertaining to the physiological signal acquired.

The sensors of the present invention can be any type known in the art for acquiring physiological signals from a subject. Examples of such sensors include electrodes, magnetic sensors, and the like. For more embodiments, the sensors are preferably electrodes designed for acquisition of the particular physiological signal being acquired. Particularly for EEG signals, the area of electrode placement may need to be prepared prior to placement of the electrode in order to remove any obstacles (e.g., dry skin, hair, or the like) that may inhibit secure electrode placement. Electrolytic fluids may also be applied to the electrode or to the subject's skin in order to increase conductivity and facilitate physiological signal acquisition. Electrodes such as those described in U.S. Pat. Nos. 8,515,522, 8,594,763, 8,805,469, 8,909,317, U.S. patent application Ser. No. 14/324,719, U.S. patent application Ser. No. 15/533,473 and U.S. patent application Ser. No. 17/701,944 all describe various electrode embodiments that minimize the effort required to prepare and apply electrodes to a subject's skin, and are hereby incorporated by reference. Skin preparation for electrode placement brings about other issues that may interfere with signal acquisition, particularly over time. For example, electrolytic fluid my dry out and become less conductive, thus significantly increasing impedance and decreasing signal quality. Also, it may be undesirable to clear all obstacles, particularly hair, from some placement sites, which is particularly relevant to EEG signal monitoring. Thus, dry physiological electrodes, such as those described in U.S. Pat. Nos. 6,782,283; 6,785,569; 7,032,301; 7,032,302; and 7,786,864 and U.S. patent application Ser. No. 13/826,185, which are hereby incorporated by reference, can be used with the present invention to provide improved electrodes with surface features that help minimize the need for electrode placement preparation while still providing conductivity and signal quality. Preferably, the electrodes are connected to the signal acquisition hardware by electrode leads that transmit the raw physiological signal from the subject to the acquisition system. Preferably, these electrode leads are shielded to help minimize perturbances of the physiological signal from outside frequencies and electrical interference such as those caused by other equipment being utilized in the vicinity of the system, ambient electronic equipment, and the like.

The signal acquisition circuitry of the various system or device embodiments of the present invention includes various electronic circuit components that are designed and combined in in order to provide preprocessing functionality to prepare the raw physiological signal for further processing and analysis. The acquisition circuitry preferably includes at least one hardware filter for rejecting high frequency interference from the raw signal. More preferably, a series of filters are used to ensure rejection of all unwanted portions of the signal, such as noise, artifacts, and other interference. Physiological signals, and especially EEG signals, are typically comprised of very low frequencies (e.g., EEG signals are typically between 0.5 Hz to about 70 Hz, but can expand to between 0.125 Hz to about 120 Hz) compared to other signals or to the various artifacts, noise and interference. Thus, filters can typically be utilized to reject frequencies greater than that range. The present invention preferably utilizes a special filtering element designed to maintain high input impedances for the common-mode signal but which still allow the lower-frequency physiological signal to pass through. Typical filters and acquisition circuitry cannot maintain this duality.

The present invention's acquisition circuitry preferably comprises an electrical circuit configuration that embodies the system with the high input impedance necessary for creating a high CMRR, while also providing the low-pass filtering capability to allow the physiological signal to pass through without perturbation. The simplest form of this circuitry comprises at least two bootstrapped capacitors and a resistor configured such that the first capacitor and the resistor form the low-pass filter and the second capacitor acts as a shunt capacitor to aid in the rejection of high frequency signals and the common-mode signal. This configuration can be repeated in the system, preferably at least one such configuration for each input lead. As the raw acquired signal passes through the input leads into the acquisition circuitry, both the lead and the shield are driven by a signal. Most systems drive the shield with the common mode signal while the lead is driven by the physiological signal potential. The present invention, however, drives both the lead and the shield with the same potential. This minimizes the amount of noise in the physiological signal because both the lead and the shield have the same potential, and this further increases the input impedance required for high CMRR of the system. Once the signal enters the input circuitry comprising the above configuration, the second capacitor is driven to have substantially the same AC voltage for both the upper and lower end of its range. With the upper and lower end substantially the same, the capacitor significantly reduces the current flow through the capacitor, while the first capacitor and the resistor maintain their low-pass filter capabilities. Therefore, as the physiological signal passes through the circuitry, low frequency signals (i.e., those below the cutoff frequency of the low-pass filter) freely pass through the circuitry, while high frequency signals are shunted to the second capacitor which removes them from the signal. This circuitry configuration effectively filters creates a high input impedance system that changes the function of the capacitors based on the signal frequency and the gain in order to remove common-mode signal and high frequency artifacts, noise and interference while allowing the low frequency physiological signal to pass without being further perturbed by the filtering process.

It is known that a Wheatstone bridge is least sensitive when upper and lower arms have widely differing impedances, for example upper arms have very low impedances and lower arms have very high impedances. The present invention exploits this fact to develop a physiological signal acquisition analog front end that mimics a least sensitive Wheatstone bridge. Considering electrode impedances being the upper arms of the bridge, a Wheatstone bridge is formed when input impedances of instrumentation amplifier and low-pass filters are presented as lower arms. The present invention uses a technique called bootstrapping to develop high impedance filters that is used in the analog front end to make it tolerant to real world balanced and unbalanced electrode impedances, electrode leads, electrical components, and so forth.

With the above system components and circuitry configurations, the present invention further embodies various methods of acquiring physiological signals from a subject. One step of a plurality of method embodiments includes using at least one sensor to measure a subject's brain wave signals over a period of time. The brain wave or EEG signals can be obtained by any method know in the art, or subsequently developed by those skilled in the art to detect these types of signals, but preferably for the present invention utilizing the system described herein. Sensors include but are not limited to electrodes or magnetic sensors. Since brain wave signals are, in general, electrical currents which produce associated magnetic fields, the present invention further anticipates methods of sensing those magnetic fields to acquire brain wave signals similar to those which can be obtained through for example an electrode applied to the subject's scalp. The subject(s) referred to in the present invention can be any form of animal. Preferably the subject(s) are mammal, and most preferably human.

If electrodes are used to pick up the brain wave signals, these electrodes may be placed at one or several locations on the subject(s)' scalp. The electrode(s) can be placed at various locations on the subject(s) scalp in order to detect EEG or brain wave signals. Common locations for the electrodes include frontal (F), parietal (P), anterior (A), central (C) and occipital (O).

In order to obtain a good EEG or brain wave signal it is desirable to have low impedances for the electrodes (not to be confused with the desired high input impedance required for high CMRR). Typical EEG electrodes connections may have impedance in the range of from 5 to 10 K ohms. It is, in general, desirable to reduce such impedance levels to below 2 K ohms. Therefore a conductive paste or gel may be applied to the electrode to create a connection with impedance below 2 K ohms. Alternatively, the subject(s) skin may be mechanically abraded, the electrode may be amplified or a dry electrode may be used. More preferably, dry physiological recording electrodes as described above may be used with or without application of electrolytic fluid, gel or colloid. Dry electrodes provide the advantage that there is no gel to dry out, no skin to abrade or clean, and that the electrode can be applied in hairy areas such as the scalp.

Additionally if electrodes are used as the sensors, preferably at least two electrodes are used—one measurement electrode for acquiring a measurement physiological signal, and one reference electrode; and if further physiological, or more particularly EEG or brain wave signal, electrodes are desired the number of electrodes required will depend on whether separate reference electrodes or a single reference electrode is used.

Once the patient is correctly attached to the EEG monitoring system then each electrode that has been attached to the subject can acquire and transmit an EEG signal to the processor. Each of the measurement electrodes transmits a measurement EEG signal which is compared against the corresponding reference electrode signal. These signals can be used to calculate a quantitative index of the particular physiological signal activity (e.g., QEEG index relating to brain or cortical activity for each hemisphere of the subject's brain, as taught in U.S. Pat. No. 8,838,226, herein incorporated by reference).

Another step of various embodiments of the present invention includes measuring physiological signal activity, such as brain or cortical activity. In order to measure the brain or cortical activity from the raw EEG signal, that signal must be "pre-processed" in order to get it into a form that is measurable and which can provide the pertinent information. Generally, pre-processing steps include signal amplification, initial hardware filtering methods, artifact detection and removal, analog-to-digital conversion, further software filtering, and the like. Physiological signals generally need to be amplified because the raw signals are typically at very low strength levels that can be difficult to discern. Amplification magnifies the signals so that they are more manageable to the particular equipment. Initial hardware filtering methods are used to try to minimize or eliminate any ambient signal interference (e.g. electromagnetic interference) that can corrupt the desired signal and prevent accurate signal analysis. Additional filtering such as artifact detection processes identify further signal perturbations including, but not limited to other signals such as electromagnetic interference that was not filtered out, and in the case of EEG monitoring, other physiological signals such as EMG, EOG, ECG, and the like. In addition, head or body movements can result in EMG artifacts that need to be removed as well. Along with detecting these artifacts it is necessary to try and remove them to leave only the unperturbed, raw signal that is desired, the EEG signal. Digital signal conversion is also required in order to take the raw physiological signal and transform it into an electrical signal that can be measured, analyzed and recorded by the given hardware. Digital signal conversion can take place also before some or all of the filtering. Once the signal has undergone both filtering and conversion from analog to digital it is then ready to undergo the appropriate and necessary analytical and analysis techniques.

Utilizing the circuitry described herein, the present invention filters the physiological signal in order to remove the high frequency artifacts, noise and interference, as well as the common mode signal while minimizing perturbation of the physiological signal as it passes through. Both the shield for each of the leads and the leads themselves are driven by the same potential, rather than driving the lead with the physiological signal potential and the shield with the common mode signal potential. The signal passes from the electrode or sensor, through the lead and enters the acquisition or front-end circuitry designed for pre-processing of the signal. A first capacitor and a resistor are utilized to form a low-pass filter with a cutoff frequency based on the useful and physiologically relevant frequencies (bio-band) of the particular physiological signal being acquired. A second capacitor is driven or forced such that the upper and lower ends of its useful range approach each other and effectively become substantially the same. Thus, the physiological signal enters into the acquisition or front-end circuitry and enters the filtering element where high frequency signals or portions of the signal such as common mode signal, artifacts, noise and other interference are blocked by the low-pass filter and the bootstrapped capacitors while the low-frequency desired physiological signal is allowed to pass through to the later stages and processed and analyzed. This filtering step has the added benefit of ensuring a high input impedance which increases the common mode rejection ratio and has an improved rejection of the common mode signal while not adding perturbation to the passed physiological signal.

Analytical and analysis techniques are needed to measure critical features of the EEG signal. Such signal analysis may allow quantification of the physiological signal activity or a component of the physiological signal. Examples of analytical results of an EEG signal may include QEEG indexing of the subject's brain or cortical activity, depth of anesthesia or sedation, wakefulness and awareness, anesthetic state and the like. These analytical and analysis techniques can include the use of spectral and higher order spectral analysis, wavelets, auditory or somatosensory evoked potentials, and the like. Analytical techniques can include but are not limited to the use of transforms for analyzing and measuring various features of the signal. Different transforms that may be used are Hilbert transform, short-time Fourier transforms, Wigner distributions, Radon transform, Fast Fourier transform, wavelet transform and the like. The most common technique is the use of spectral and higher order spectral analysis such as Fast Fourier transform. The preferred technique is the use of wavelet transform.

Several embodiments of the present invention may involve a step transmitting physiological signal data and or/indices from the processor to another device such as a monitor for display, a storage device, or a remote device for review by a clinician. The processor calculates the physiological signal indices, such as brain or cortical activity indices, substantially in real time as it receives the EEG signal from each electrode attached to the subject, and transmits those indices to a monitor for display. This occurs as an electrical signal from the processor containing the current QEEG index relating to brain or cortical activity for a given brain hemisphere which is sent along video connection wires which are attached to the monitor that displays the resultant visual depiction of the indices.

Alternatively, the signal could be broadcast wirelessly from the processor via WiFi network, or a medical band or Bluetooth RF connection to a monitor equipped to receive such signals. The physiological signal data, including for example brain or cortical activity indices, can be transmitted from the processor to a monitor via these or any other currently available communication methods for visual displays or any that may become available in the future.

Preferably, when using a radio frequency method the system will transmit data in a frequency range, or band, such that it will not receive interference from other radio frequency signals. Preferably, the system will transmit below a frequency of 2.0 GHz to avoid frequency bands that are highly congested, namely the 2.4 GHz band. Operation within these bands over 2.0 GHz may make interference problematic such as by limiting usable bandwidth. Additionally, if power is constant then operation at lower frequencies allows for greater operational range than at higher frequencies. Conversely, operation at lower frequencies consumes less power than higher frequencies over the same range.

Now referring to the drawings, FIG. 1 is a block diagram of a system for monitoring and real-time therapy applications, including the acquisition circuitry of the present invention for improved filtering of physiological signals. The system can be connected to the subject or patient either on the subject or patient's scalp with mounted individual surface electrodes 100 or an electrode array 100a, intracranial cortical grids 110, or implanted deep brain electrode(s) 115 depending on the embodiment. The electrode leads 100b are preferably connected to the system via a yoke 105 connected to front-end acquisition circuitry 195 containing various filters other hardware designed to reject high frequency noise, interference, and other undesired portions of the signal, for example cardiac defibrillation resistors (not shown) designed to absorb the energy of a cardiac defibrillation pulse. This circuitry 195 and the associated electronics in the front-end of the instrumentation amplifiers is designed to protect the instrumentation electronics and in particular applications to have electromagnetic interference filters (EMF) to eliminate interference caused by other electrical devices, while still ensuring that most of the energy delivered by the pulse is used for the intended therapy. This circuitry 195 is where the herein described filtering apparatus is located comprising the bootstrapped capacitors and low-pass filters designed to reject common mode signal, noise and interference from the physiological signal while allowing the physiological signal to pass through substantially unperturbed for further processing and analysis. The brainwave signals are then amplified and digitized by an analog-digital converter (ADC) circuitry 135.

In addition, a signal quality (SQ) circuitry 125, 130 can be used to provide measurement currents to the leads in order to calibrate the instrumentation amplifiers and measure electrode impedance. Similar SQ circuitry monitors the front-end amplifiers in order to detect eventual saturation that occurs when leads 105 are disconnected. This information, along with the digitized brainwave signals, is relayed to the processor 140-170. Optionally, but preferably, an electrode impedance module may be included in the processor. The electrode impedance module is the portion of the processor which embodies the present invention and thus provides an electrical current to the electrodes as described above, and measures the resultant electrical impedance to determine the quality of the signal being supplied through each electrode.

The processor is composed of the sub-systems 140 thru 170. The signal quality assessment module 140 is used to check whether each signal acquired by the system is of sufficient enough quality to be used in the subsequent analysis. Generally, signal quality assessment is carried out by two main steps: first, by removing noise and interference and is performed partially by the front-end circuitry 195, and partially through software processing, and second by substantially continuously measuring the electrode impedance of each brainwave channel. Once high frequency noise and interference has been removed by the front-end circuitry 195, the signal passes through but still may have additional noise or interference components. In particular, one key area for noise in signal quality is in the 50 to 60 Hz range produced by a poor electro-magnetic environment about the electrodes or the device. At high levels of 50 or 60 Hz indicate either a poor electro-magnetic environment, or a poor connection to the subject or patient which will result in a heightened sensitivity of the system for any other environmental noise (e.g., lead movement, vibration, etc.). High levels of 50 or 60 Hz noise are usually indicative of poor signal quality. If signal quality is low (regarding the present invention, the electrical impedance of electrode[s] is too high), the user has several options. Electrodes can be replaced, conductive gel can be reapplied, or the electrode can be slightly moved and/or the skin re-abraded to renew the signal quality.

If the signal quality and electrode impedance are good, the system preferably proceeds by analyzing the acquired signals in order to detect the presence of environmental or physiological artifacts, which may be corrupting the signal. This analysis is done in the artifact identification and measures computation module 145. Preferably, several artifact detection methods or algorithms are used in combination. These artifact detection methods or algorithms analyze the signal for artifacts using combinations of both sensitivity specific and specificity specific methods or algorithms, each detecting the presence of artifacts in different ways, and those measures are combined to increase the accuracy of artifact detection in the combination and decision module 150. Other artifact detection techniques may be used as well in the system, devices or methods of the present invention. Some artifacts, such as ocular artifacts, can be removed from the signal by using a de-noising method. This is done at the level of the artifact detection & removal module 155.

De-noised and artifact-free signals are sent to the brainwave analysis/processing module 160. This sub-system derives information contained in the signal, such as the level of consciousness or cortical quantification of the subject or patient, the presence of electro-cortical silence and abnormal brain/cortical activity such as seizure, ischemia, aneurysm, etc. This information can be used to identify one or more brain/cortical abnormalities as well as quantifying brain/cortical activity in general for the subject or patient.

The automated detection & decision module 165 is where the processed signal is analyzed to determine the presence of any brain/cortical activity abnormalities that may be present. It uses a method that amplifies abnormal spike activity in the signal, while minimizing the background 'normal' brain activity. It also combines the real-time seizure index with the information obtained in the brainwave analysis/processing module 160 in order to provide an accurate diagnostic of the subject or patient's brain state.

A user interface module 170 provides the means for the user to interact with the system. In the preferred embodiment, this is done through the use of a display 180, which can be a touch screen display. The display 180 is used to warn the user, in real-time, of the presence of poor signal quality, abnormal brain (or other physiological) activity, general system and subject information, and the like. In addition, the user interface module 170 may archive some or all of the acquired signals and processed variables into a mass storage device 175, for later review.

The mass storage device 175 is used as a long term storage archive for all of the acquired EEG signals as well as the accompanying processing results. These data will then be available for later use. The signals will then be available for historical use and review where clinicians or researchers can check for artifacts or other abnormal brain activity; for example, seizures and the like. A raw EEG signal or an artifact free EEG signal can be stored in the mass storage device 175 or a corrupted signal can be stored as well with the artifacts identified as part of the signal. Furthermore, they can be used as a database from which signals can be used for baseline determination or calibration of artifact detection techniques.

Finally, in some embodiments, the system is connected to a mechanism that semi-automatically or automatically delivers a treatment to the subject or patient, referred in the schematic as the treatment delivery device 190. The output of the system through a processor can be used with the treatment delivery device including a processor in closed loop, partially closed loop or open loop to automatically deliver physical, electrical or chemical treatment to the subject or patient automatically based on the occurrence of abnormal brain activity, and monitor the effectiveness of such treatment in real time 185.

Figure 2:
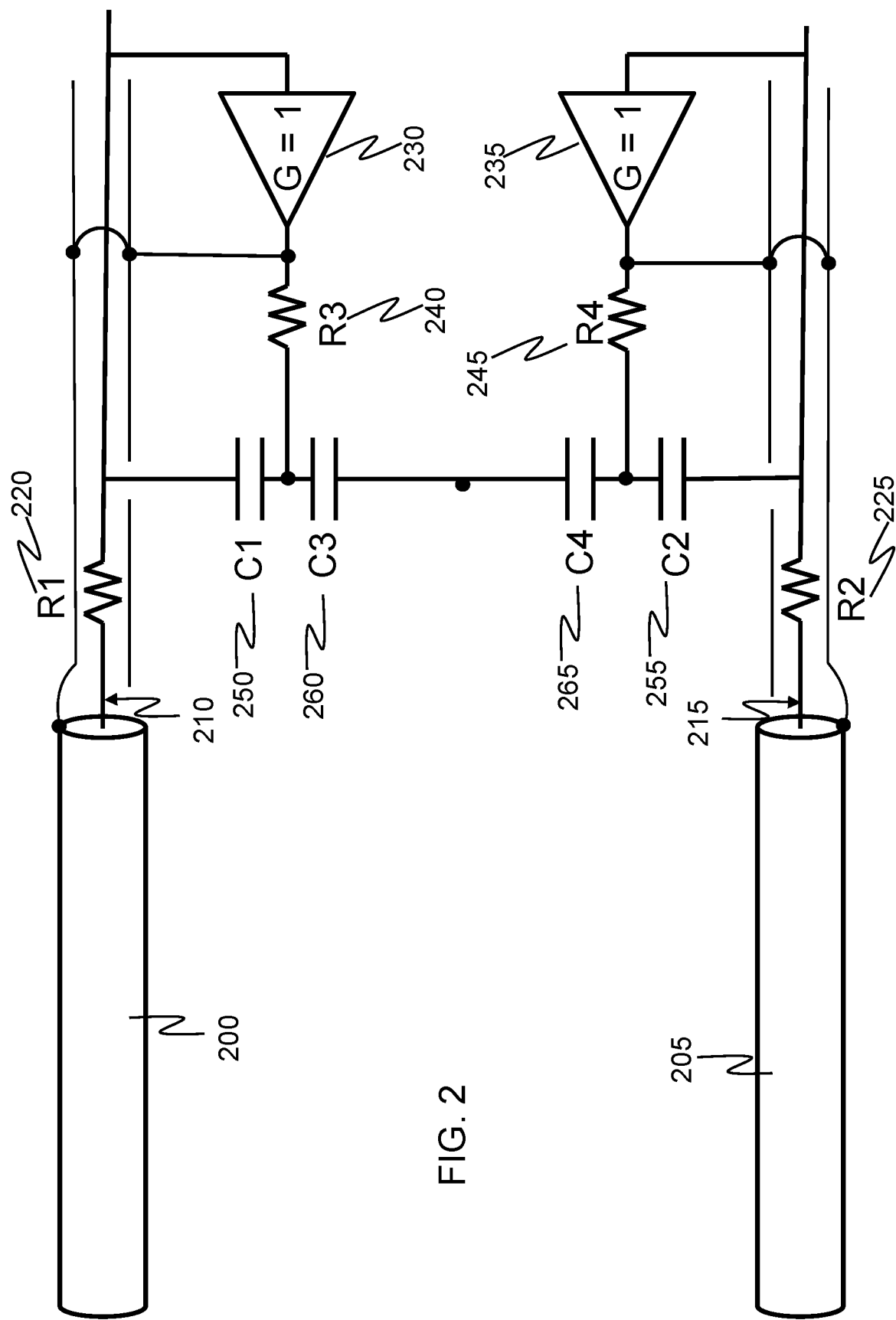
FIG. 2. Electrical schematic of an embodiment of the acquisition circuitry of the present invention.

FIG. 2 is a schematic of one embodiment of the front-end acquisition circuitry of the present invention. The schematic depicts two electrodes or sensor lead cables each comprising shielding 200, 205 and an internal electrical lead 210, 215. The shielding for each lead is preferably driven with the same electrical potential unity-gain buffer as the electrode lead itself, as opposed to with the common mode signal as is commonly done, in order to help remove noise from the signal. These leads transmit the physiological signal from the electrodes or sensors (not shown) attached to the subject, and into the acquisition circuitry comprising a series of electrical components designed and arranged to filter the signal and remove undesired noise, interference, artifacts and the like, including common mode signal. The input filtering components of the present invention, for each lead, comprise a pair of boot strapped capacitors (C1 250 for the first lead, and C2 255 for the second lead), and a resistor elements (R1 220 and R3 240 for the first lead, and R2 225 and R4 245 for the second lead). Capacitor C1 250 and resistors R1 220 (C2 255 and R2 225) combine to form a low-pass filter designed to remove all signal portions above the cutoff frequency of the filter and allow the portions of the signal with frequencies below the cutoff frequency to pass through. The lower end of C1 250 (C2 255) is driven by buffer 230 (235) to the same potential as of the upper end and hence greatly reduce the flow of electrical current through C1250 (C2 255). This bootstrapping of the capacitors 250 and 255 serves to increase the input impedance of each lead, which significantly raises the CMRR for each lead. This effectively means that more common mode signal is rejected while more of the desired physiological signal is allowed to pass through. Meanwhile, the low-pass filter operates to remove other forms of interference and noise. Thus, the circuitry operates to remove common mode signal, noise, and interference of many forms without perturbing the underlying physiological signal, and allowing that physiological signal to pass through for further processing and analysis.

Figure 3:
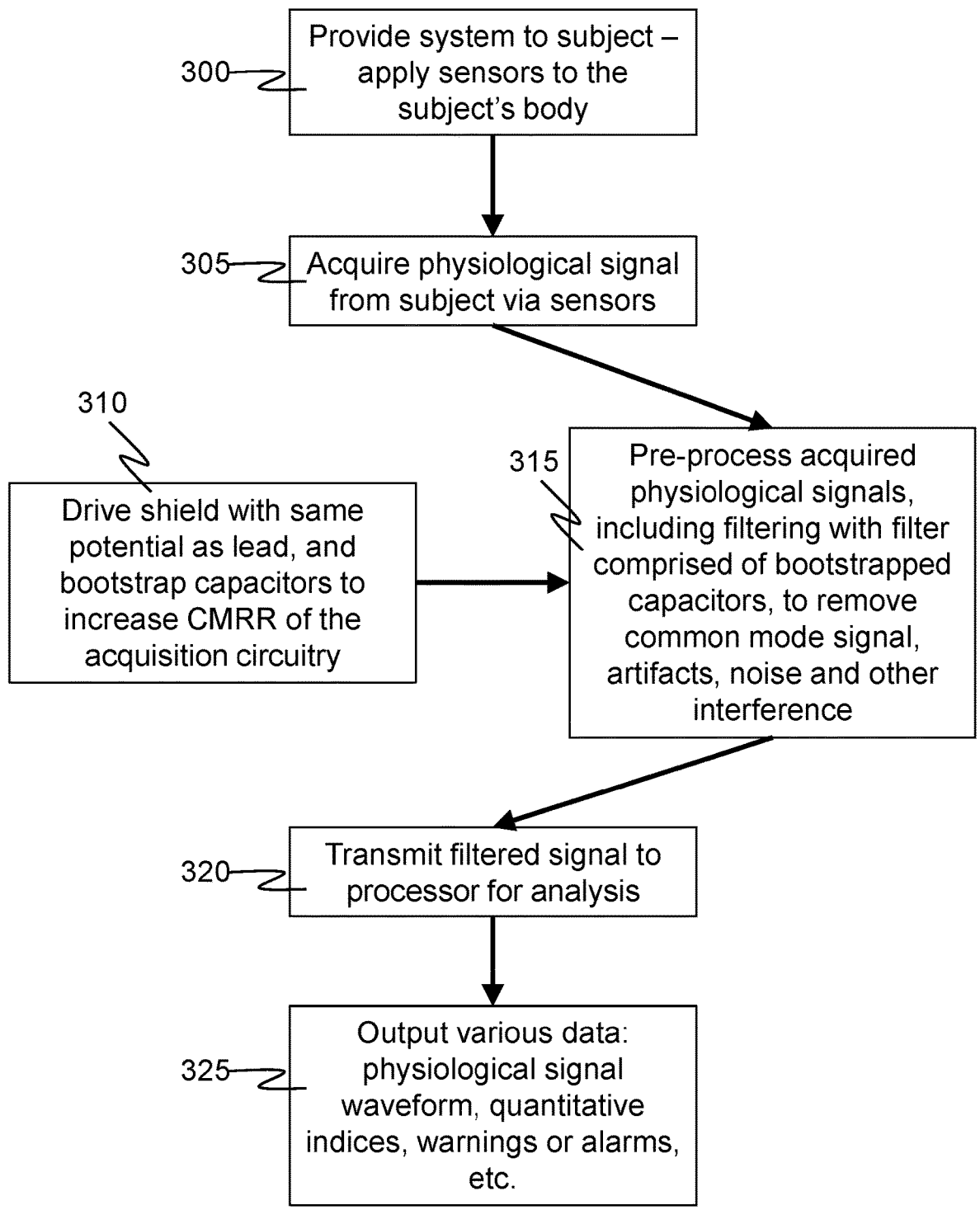
FIG. 3. Flow chart depicting an overview of various methods of the present invention utilizing the acquisition circuitry of the present invention to pre-process physiological signals FIG. 4. Picture depicting an example of data output for a bilateral EEG acquisition system utilizing the acquisition circuitry and methods of the present invention.

FIG. 3 is a flow chart for an overview of various method embodiments of the present invention. The first step is to provide a system 300 as described herein and apply electrodes or other sensors to the subject's body according to arrangements appropriate for acquiring the desired physiological signal. The system is then used to begin, and likely continue, acquiring a physiological signal 305 from the subject. The front-end acquisition circuitry is arranged and driven 310 in order to provide the beneficial filtering capabilities described herein. First, the shields of each lead are driven with the same potential as the leads themselves which helps to reduce noise caused by different potentials. This is significant given that typically the shielding is driven by the common mode signal, which creates a difference in potential between the shielding and the leads, and causes noise. The present invention reduces this effect. Further, a second capacitor for each lead, as described above, is driven such that the upper and lower ends of its range become substantially the same, thus significantly reducing the flow of electrical current through that capacitor. These second capacitors are bootstrapped with first capacitors for each lead, where the first capacitors combine with a resistor to form a low-pass filter. This arrangement effectively raises the CMRR for the input leads and circuitry, and creates an improves filtering process for removing not only noise and interference, but common mode signal as well. Thus, with the input acquisition circuitry driven 310 accordingly, the physiological signal passes through said circuitry and is pre-processed 315 in a manner to filter out the unwanted common mode, noise, interference, artifacts, and the like from the physiological signal. The filtered physiological signal is then transmitted 320 to the processor for further software processing. Ultimately, various forms of data and information relating to the physiological signal are output 325 to a display and/or stored for later review and analysis. Such data may include the waveforms of the physiological signal, quantitative indices relating to the physiological signal, signal quality information, system information, subject information, and the like.

Figure 4:
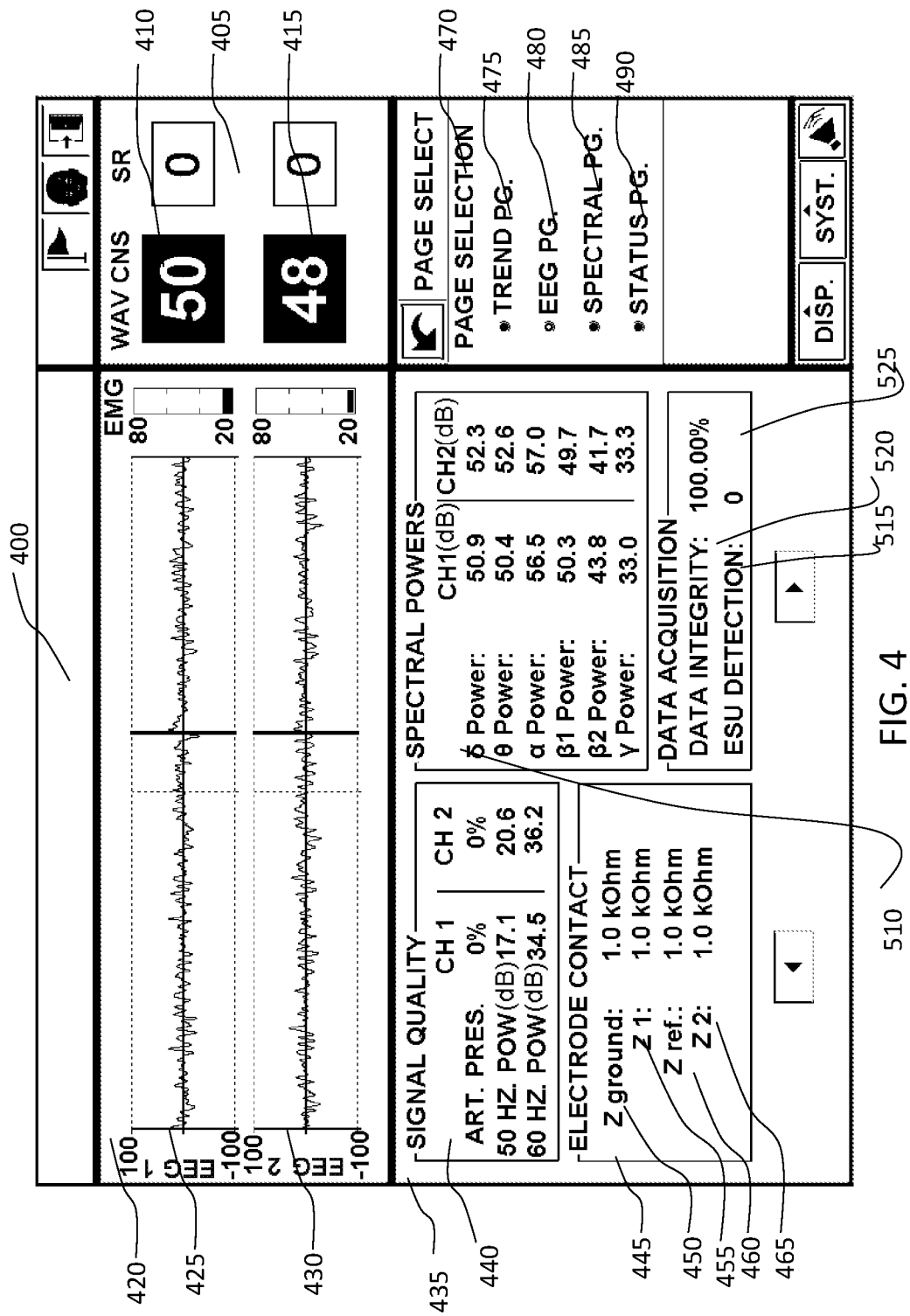

FIG. 4 is an example of one embodiment of a display showing various output data relating to the filtered and pre-processed physiological signal. In this display 400, for a system used to acquire electroencephalographic (EEG) signals, individual brain or cortical activity indices 410, 415 for each brain hemisphere are shown in the upper right portion 405 of the display 400 displayed in color (not shown).

The individual raw EEG waveforms 425, 430 for each brain hemisphere are displayed in the upper left portion 420 of the display 400. If a spike is recorded in one of the hemisphere EEG waveforms displayed indicating that some brain or cortical activity has occurred, the corresponding brain or cortical activity QEEG index would also rise indicating a higher level of consciousness, wakefulness or awareness than expected.

A general status page is shown in the lower left portion 435 of the display 400 with various indicator views and measurements displayed simultaneously, such as signal quality 440, electrode contact 445, spectral powers 510, and data acquisition 525. This optional view portrays to the caregiver multiple information sources regarding various aspects of the EEG signal acquisition process, all at the same time, rather than choosing one or two displays at a given time. Each of these sub-screens gives a textual overview of some portion of the EEG signal or measurement process that can be shown in greater detail or in graphical form in some other optional display described in several of the other figures.

One such indicator view is the signal quality portion 440 of the status page 435. This portion displays measurements for both EEG electrodes being collected, each electrode corresponding to one of the subject's brain hemispheres. Various measurements regarding signal quality can be displayed here including, but not limited to, the presence of artifacts in each electrode's signal and the spectral power of each electrode at various frequencies.

Another indicator view is the electrode contact portion 445 of the status page 435. This measurement is closely related to signal quality, but focuses on the fidelity of the connection between the electrodes or other sensors and the subject's body. The system performs this measurement as a function of the electrical impedance of each electrode or sensor. The system then displays the measured impedance value for each of the electrodes or sensors used: grounding electrode 450, first measurement electrode 455, reference electrode 460, and second measurement electrode 465. This electrode impedance is not the same as the input impedance discussed herein with respect to CMRR and removal of undesired signal portions. Electrode impedance is the impedance of the electrode-skin contact, whereas the input impedance for CMRR purposes is impedance of the electrode leads, as represented by R1 220 and R3 225 of FIG. 2.

Yet another indicator view is the spectral powers measurement portion 510 of the status page 435. This portion displays measurements for both EEG electrodes being collected, each electrode corresponding to one of the subject's brain hemispheres. Various measurements of the spectral powers of the EEG signal from each hemisphere of the subject's brain can be displayed here. The powers of each spectral band or wavelet of the original parent EEG waveform are displayed.

Still another indicator view is the data acquisition portion 525 of the status page 435. This portion displays measurements regarding the quality of the data being recorded by the system from the EEG signal from each hemisphere of the subject's brain. The system can determine the level of data integrity 520 and display that in the data acquisition window, as well as the detection of electrostatic units 515 that may be detected and potentially interfere with the data acquisition and decrease the quality integrity of the recorded data.

The lower right portion of the display 400 presents a selection menu 470 which gives the caregiver options for different views or embodiments to employ. The caregiver can select to display a trend page (not shown) by selecting the Trend Page button 475. The caregiver can select to display an EEG waveform page (e.g., 420, but enlarged) by selecting the EEG Page button 480. The caregiver can select to display a spectral page (not shown) by selecting the Spectral Page button 485. The caregiver can select to display a status page (not shown) by selecting the Status Page button 490. By selecting one of these buttons, the display 400 would be altered to include the selected page.

All of these forms of data output and display are a result of further analysis of the pre-processed signal. The filtering and pre-processing of the circuitry described herein removes a larger portion of unwanted signal portions, including common mode signal, noise, interference, artifacts, and the like, and allow the system to further process a much cleaner signal and therefore obtain more accurate measurements and analysis of the subject's physiological signals. The present embodiment of FIG. 4 depicts a system for bi-lateral EEG monitoring a subject's brain function of each hemisphere separately, and represents just one example of the type of system which might benefit from the improved filtering and pre-processing of the present invention.

Figure 5:
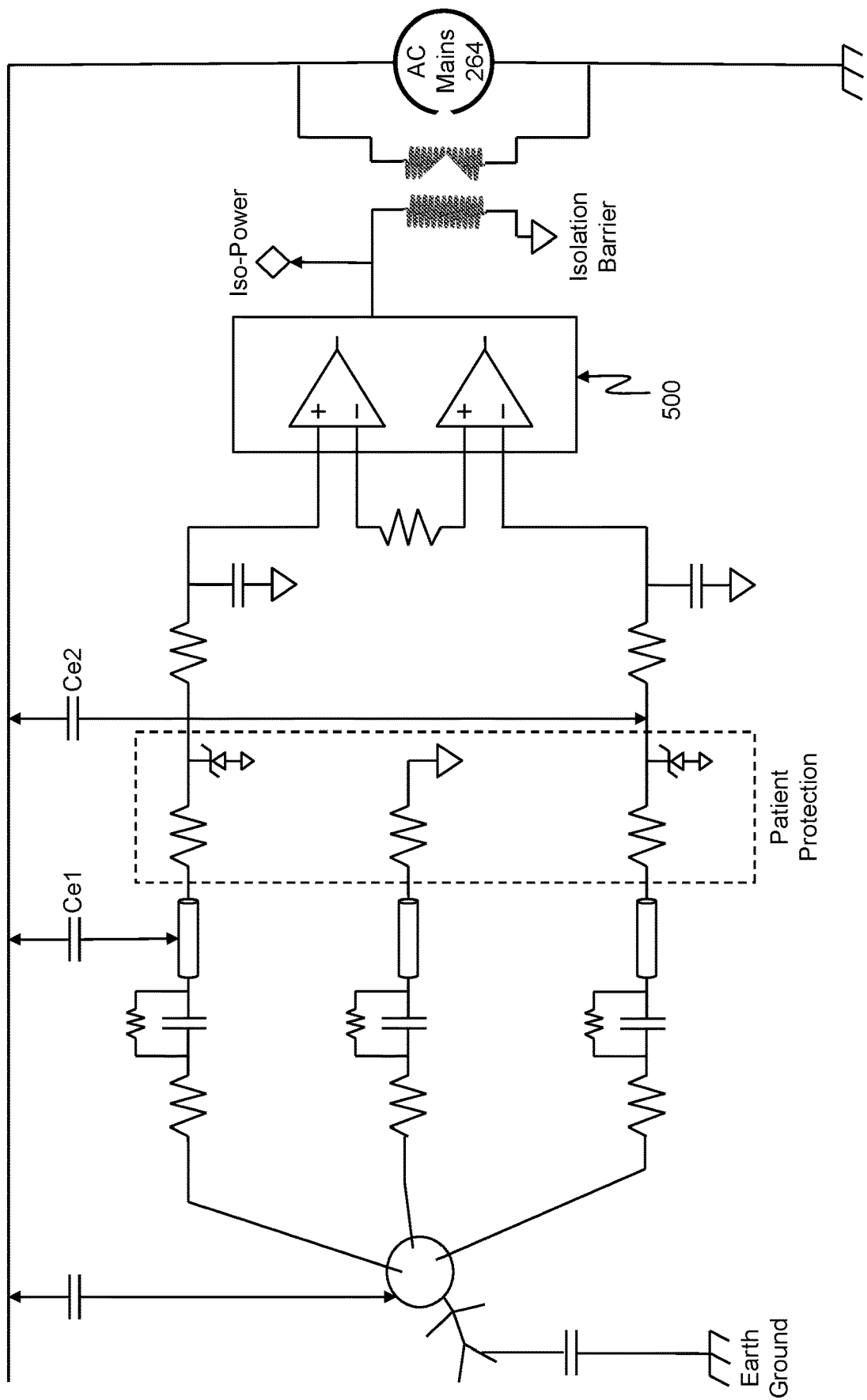
FIG. 5. Graphical representation of an exemplary physiological signal acquisition device attached to a subject and coupled with a power signal to the device.

FIG. 5 represents a schematic of a subject attached to a physiological signal acquisition device and specifically depicts how 50/60 Hz power signal can be coupled to a floating subject.

Figure 6:
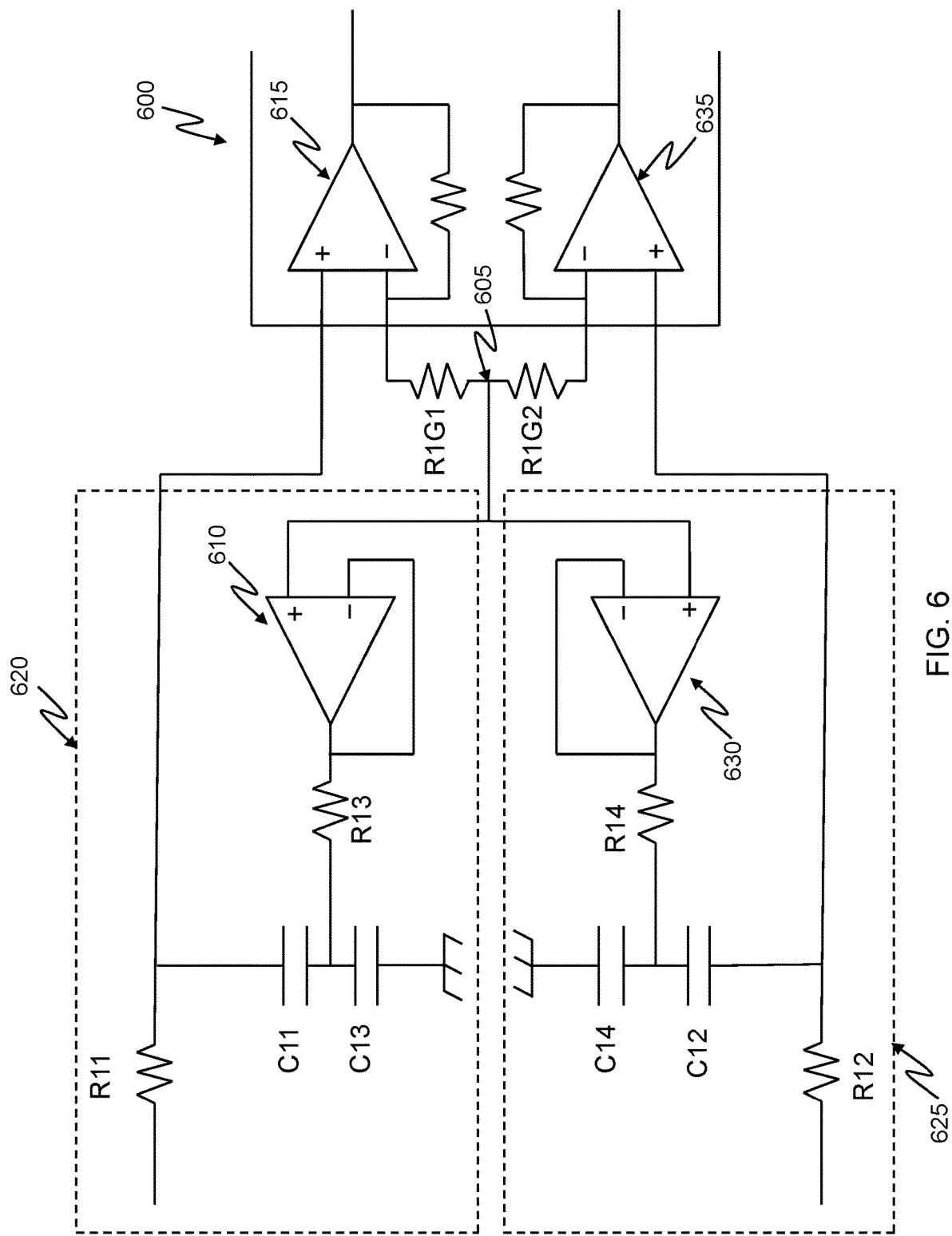
FIG. 6. Schematic depicting an embodiment of the present invention's acquisition circuitry comprising several bootstrapped filters and an arrangement of components that allows common mode signal to be removed prior to the instrumentation amplifier, and allowing for addition of multiple channels of signal using an existing channel as a reference.

FIG. 6 shows one embodiment of the acquisition circuitry of the present invention. The low-pass filter formed by elements R11 and C11 form a modified filter to bootstrap the filter capacitor C11. Additional capacitor C13 is connected in series with C11 to ground. Two gain resistors R1G1 and R1G2 instead of one, as compared typical circuits known in the art, are used and connected in series to provide a junction node 605. The junction node 605 is connected to the input of unity gain buffer 610. The output of the buffer 610 is connected to the node between C11 and C13 through filter resistor R13. The node between filter elements R11 and C11 is connected to the non-inverting input terminal 615 of the instrumentation amplifier 600.

The filter resistor R13 and capacitor C13 form a low-pass filter preferably having cutoff frequency comparable to the bootstrap filter formed by elements R11 and C11. At frequencies below the cutoff frequency, the bootstrapped capacitor C11 can effectively be made open circuit to common mode signal. Since each inverting terminal of amplifiers 615 and 635 of instrumentation amplifier 600 is at the same voltage as its non-inverting counterpart and no common mode current flows through the gain resistors, the node 605 is a node of common mode signal. Therefore, the unity-gain buffer 610 drives the lower end of C11 with the same common mode signal as the top which causes C11 to exhibit high impedance to common mode signal. Since the same node 605 is a ground for differential mode signal, the capacitor C11 exhibits its rated impedance to differential mode signal. For high frequencies above the cutoff frequency, the filter capacitor C13 becomes shorted to ground and hence enables the filter capacitor C11 to exhibit its rated impedance to both common and differential mode signals.

Since non-inverting terminal of 615 and C11 both exhibit high input impedances, the analog front line 620 exhibits high input impedance to common mode signal for passband. However, for frequencies above the cutoff frequency, where low input impedance is desirable for noise rejection, bootstrapped filter capacitor element C11 assumes its rated impedance and provides low impedance path to ground through the filter element R11 to act as a low-pass filter to prevent undesired signals from reaching the instrumentation amplifier 600.

In a similar manner, the other analog front line 625 consisting of a second unity gain buffer 630, bootstrapped capacitor C12, and filter components R14 and C14 raises the input impedance to common mode signal for pass-band while maintaining low-impedance path to ground for noise or other interference.

Figure 7:
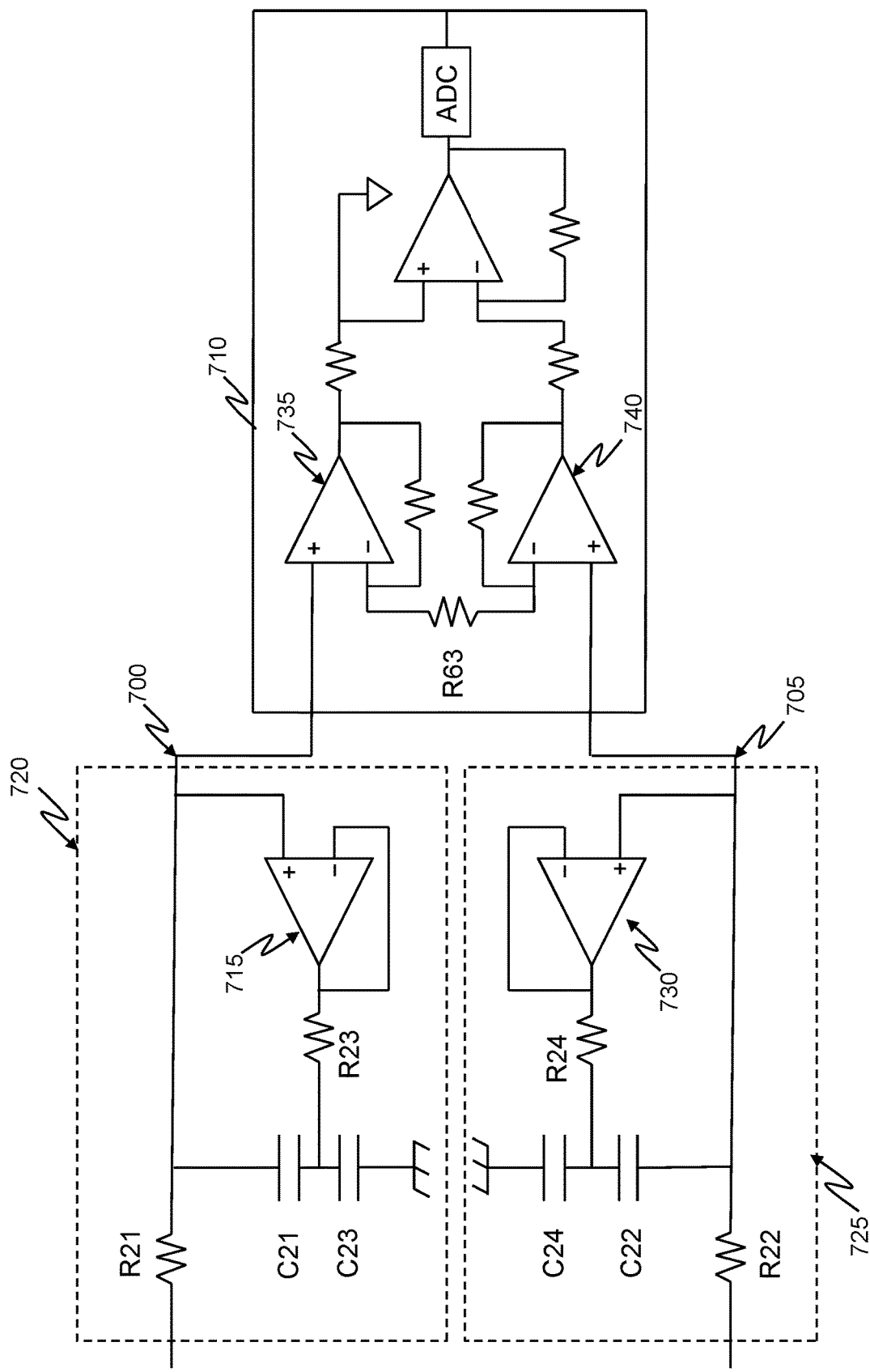
FIG. 7. Schematic depicting an embodiment of the present invention's acquisition circuitry comprising several bootstrapped filters and an arrangement of components that allows common mode signal to be removed prior to the instrumentation amplifier.

FIG. 7 shows another embodiment of circuitry of the present invention. This embodiment preferably is used when a common mode node, which is a node of common mode signal, from instrumentation amplifier is not readily accessible. The filter capacitor C21 is bootstrapped using unity gain buffer 715 and filter elements R23 and C23. Unlike the embodiment depicted in FIG. 6, the unity gain buffer input is directly connected to non-inverting terminal of amplifier 735 of instrumentation amplifier 710, which is also directly connected to the node 700 between filter elements R21 and C21.

Like the embodiment depicted in FIG. 6, the filter resistor R23 and capacitor C23 form a low-pass filter preferably having cutoff frequency comparable to one formed by elements R21 and C21. Within the pass-band, the bootstrapped capacitor C21 can effectively be made an open circuit. The buffer 715 forces the lower end of C21 to be at the same voltage as the top and hence greatly reduces the current flow through C21 to lower its effective value. On the other hand, the capacitor C23 becomes shorted to ground at frequencies above the cutoff frequency and hence enables the capacitor C21 to resume its rated value for the stop-band.

Since non-inverting terminal of 735 and C21 exhibit high input impedances, the analog front line 720 exhibits high input impedance for pass-band. However, for frequencies above the cutoff frequency, where low input impedance is desirable for noise rejection, effective filter element is simply C21 in series with C23 and provides a low impedance path to ground through R21 to act as a low-pass filter to prevent undesired signals from reaching the instrumentation amplifier 710.

In a similar manner, the other analog front line 725 consisting of a second unity gain buffer 730, bootstrapped capacitor C22, and filter components R24 and C24 raises the input impedance for pass-band while maintaining low-impedance path to ground for noise or other interference.

Figure 8:
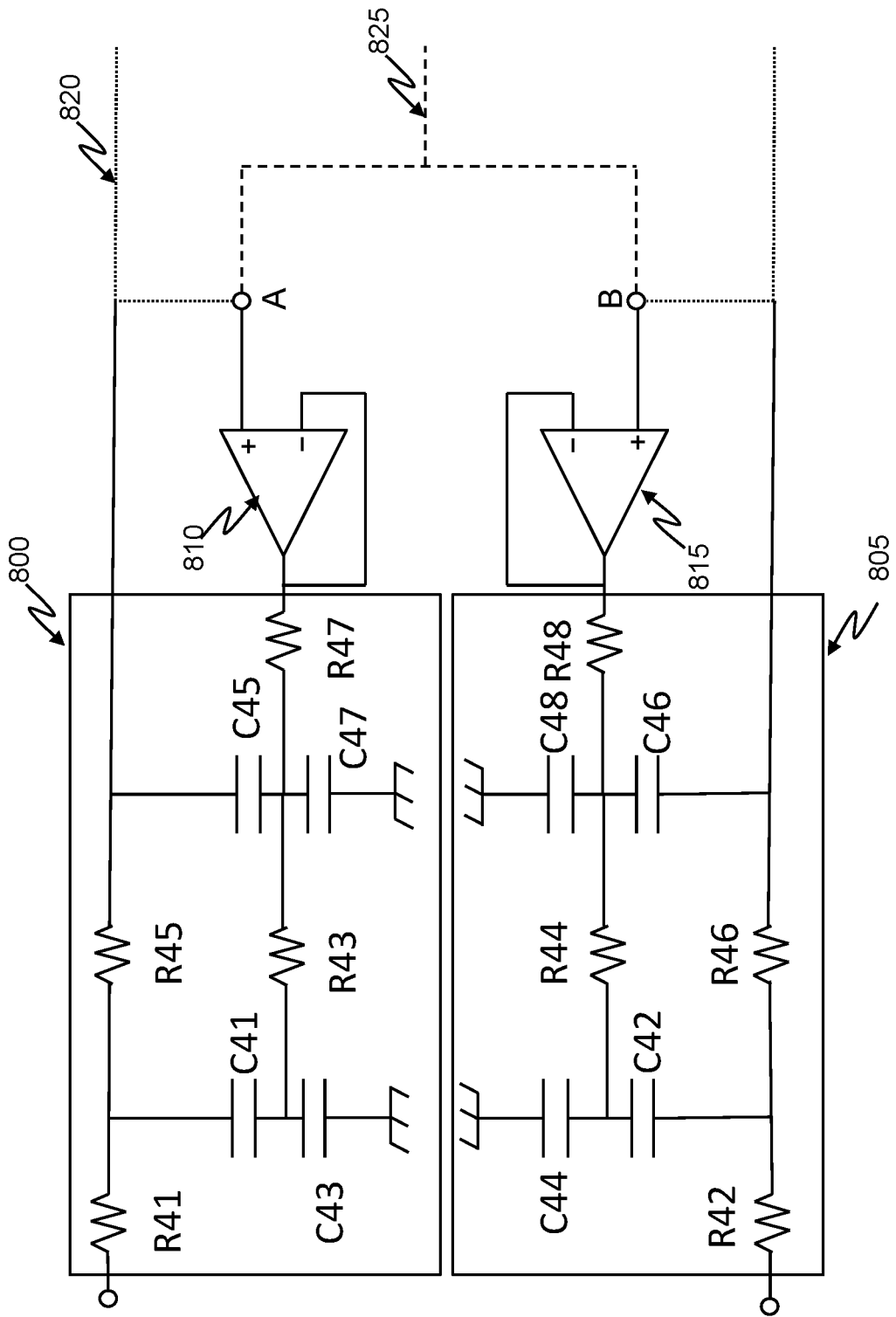
FIG. 8. Schematic depicting an embodiment of the present invention's acquisition circuitry comprising several bootstrapped filters to improve the rate of roll-off of the filters.

FIG. 8 shows another embodiment of circuitry of the present invention that is preferably used when −20 dB/decade roll-off of the low-pass filter is not adequate. Acquisition of physiological signal using a low footprint and possibly cost effective integrated solution such as TI ADS1299 is an example of such needs. The ADS1299 uses instrumentation amplifier and analog to digital converter in a single package without any anti-aliasing filter. The rate of roll-off needs to be sufficient, which depends on the sampling rate used for analog to digital converter, so that anti-aliasing effect on the acquired signal can be removed. The present embodiment uses a two-stage filter 800 to improve the rate of roll-off of the cascaded low-pass filters. The first filter stage of 800 consists of the filter elements R41, C41 and the second filter stage of 800 consists of the filter elements R45, C45. Using the same technique, both filter capacitors C41 and C45 are bootstrapped using a single buffer 810 through other filter elements R47, C47, R43, and C43. A similar two stage filter 805 is used for the second lead. The first filter stage of 805 consists of the filter elements R42, C42 and the second filter stage of 805 consists of the filter elements R46, C46. Using the same technique, both filter capacitors C42 and C46 are bootstrapped using another buffer 815 through other filter elements R48, C48, R44, and C44.

The bootstrapped filter stages can be driven by different configurations such as those depicted in FIGS. 6 and 7 with simple changes in connection between the filter stages and the instrumentation amplifier depending on the desired configuration. For embodiments where a common mode node can be obtained applying the same technique shown in FIG. 6, the filter stages 800 and 805 can be connected via a first optional pathway 825 to the instrumentation amplifier 600 such as depicted in FIG. 6 wherein two gain resistors are used instead of one compared to conventional gain configuration of instrumentation amplifier. Alternatively, for embodiments where the instrumentation amplifier does not provide any means of obtaining a common mode signal, the filter stages 800 and 805 can be connected via a second optional pathway 820 to the instrumentation amplifier 710 such as depicted in FIG. 7.

Figure 9:
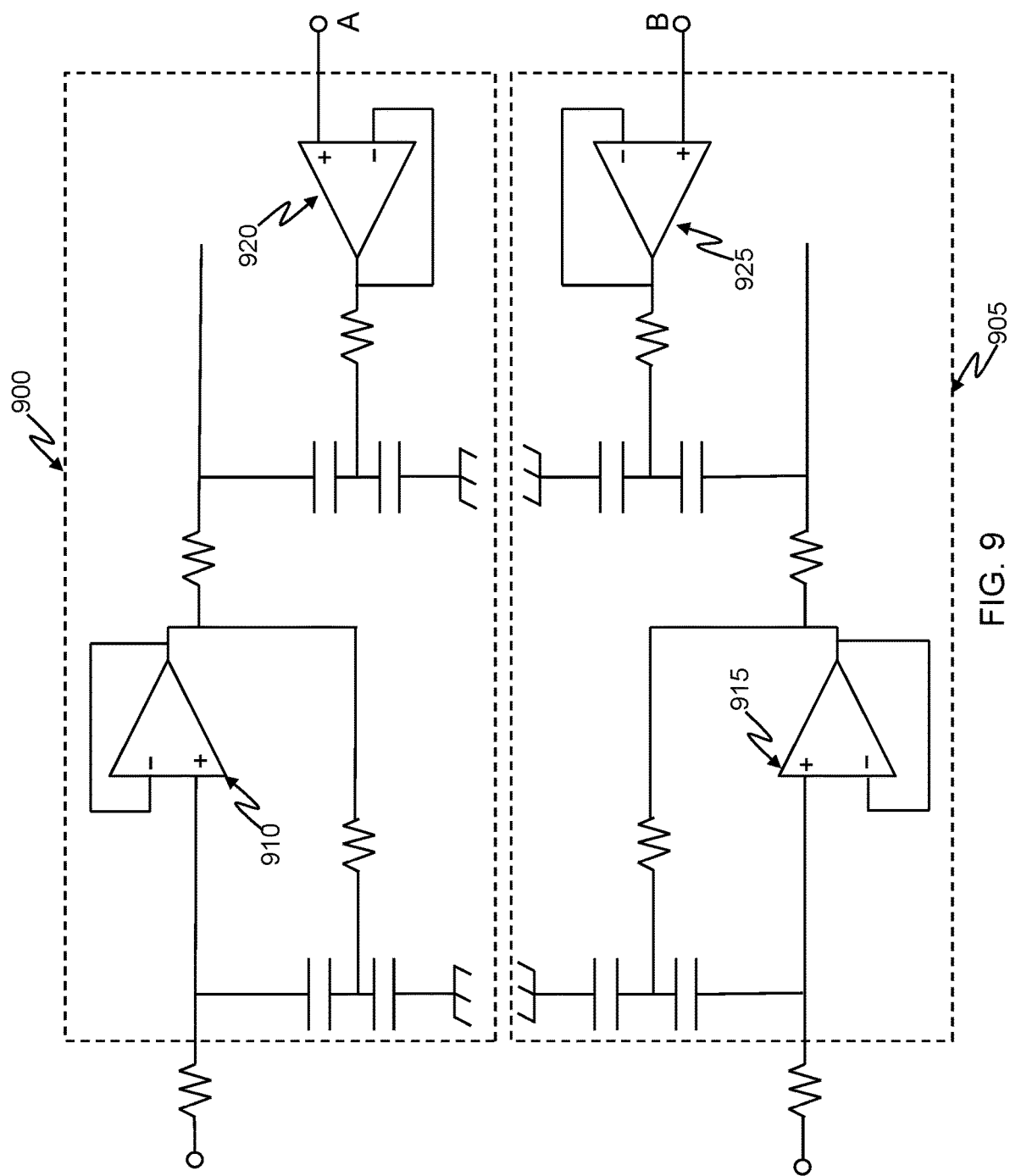
FIG. 9. Schematic depicting an embodiment of the present invention's acquisition circuitry comprising several bootstrapped filters to improve the rate of roll-off of the filters utilizing separate unity gain buffers for each filter stage.

FIG. 9 shows another embodiment of the circuitry of the present invention that is preferably used when even higher rate of roll-off is required. Compared to the embodiment shown in FIG. 8, separate unity gain buffer is used for each filter stage. Buffer 910 is used for filter stage comprising R51, C51 and buffer 920 is used for the second filter stage comprising R55 and C55. Similarly buffer 915 and 925 are used for each filter stage used for the second lead. The advantage of the additional buffer 910 (915) is that it not only bootstraps the added filter stage but also isolate the filter stage from the other. Such isolation greatly improves the rate of roll-off of the cascaded low-pass filter.

Figure 10:
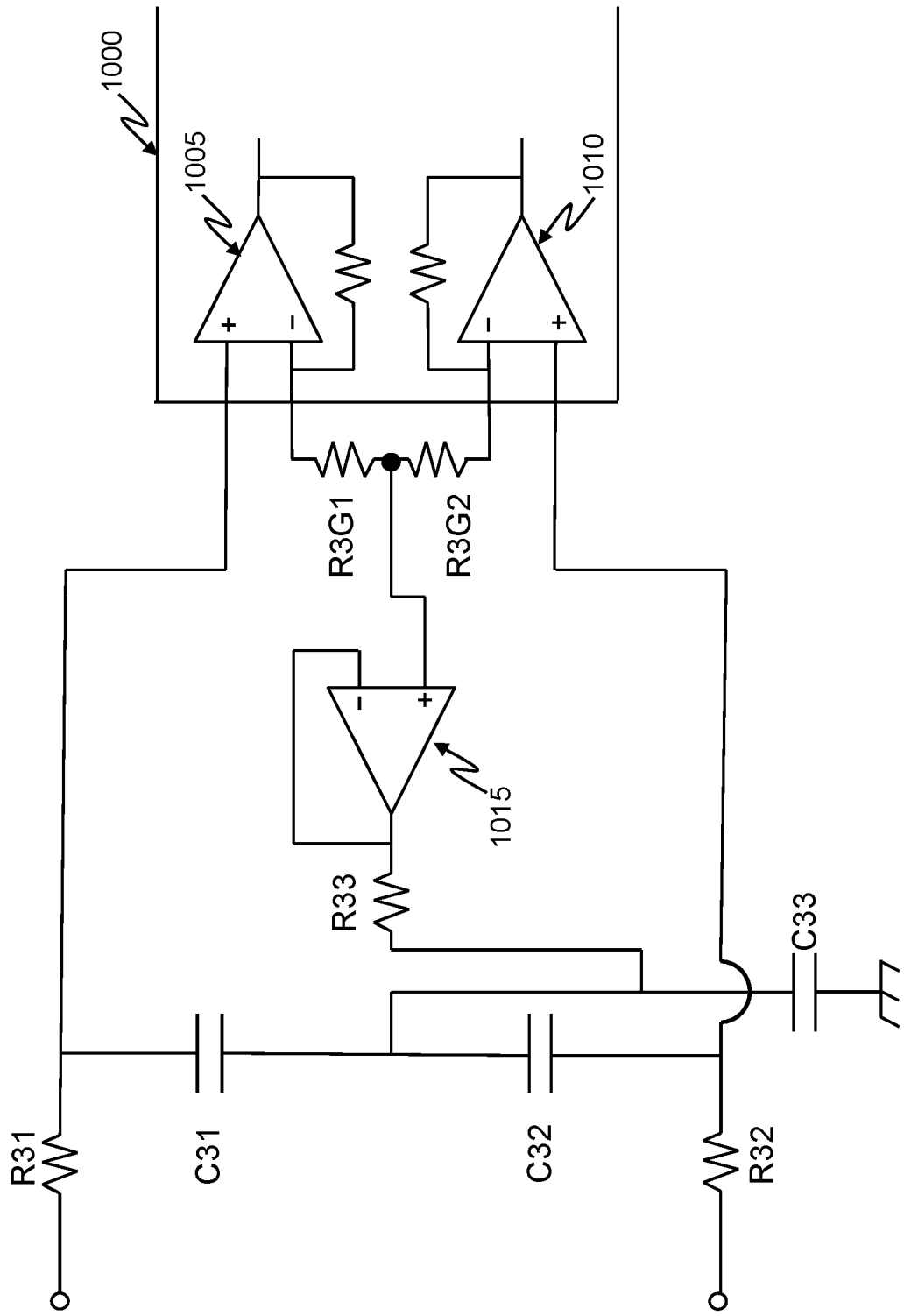
FIG. 10. Schematic depicting an embodiment of the present invention's acquisition circuitry comprising several bootstrapped filters and an arrangement of components that allows common mode signal to be removed prior to the instrumentation amplifier, and requiring complete replication of the depicted circuitry to add additional signal channels.

FIG. 10 shows another embodiment of the circuitry of the present invention that is preferably used when space and cost saving solution is needed. Like the embodiment shown in FIG. 6, two gain resistors in series are used. The first gain resistor R3G1 is connected between a first inverting terminal of amplifier 1005 of the instrumentation amplifier 1000 and the other gain resistor R3G2 which is then terminated to the other inverting terminal of amplifier 1010 of the same instrumentation amplifier 1000. The two gain resistors are preferably matched to about 0.1% tolerance. The filter elements C31 and C32 are bootstrapped using a single unity gain buffer 1015. The input of the unity gain buffer 1015 is connected to the node between gain resistors R3G1 and R3G2. A filter resistor R33 is connected between the output of the unity gain buffer 1015 and the node terminal between C31 and C32, which is then terminated to ground through another filter element capacitor C33.

In similar manner, the filter resistor R33 and capacitor C33 form a low-pass filter preferably having cutoff frequency comparable to one formed by elements R31 and C31 and also preferably to one formed by R32 and C32. At frequencies below the cutoff frequency, the unity gain buffer 1015 drives the node between the bootstrapped capacitors C31 and C32 to the same common mode potential as their top terminals so that no common mode current flows through the capacitors C31 and C32 effectively making them pose high impedance to the common mode signal. In contrary, both capacitors C31 and C32 exhibit their rated impedance to differential mode signal. For high frequencies above the pass-band, the filter capacitor C33 becomes shorted to ground and provides sufficient path to ground for filter capacitors C31 and C32 and filter resistors R31 and R32 to act as a low-pass filter to prevent noise or other interference signals from reaching to the in-amp.

Since physiological signal acquisition systems intend to acquire differential mode signal while rejecting any common mode signal, it is required that components used in one analog front line match the corresponding components of the other analog front line. For example, C11 and C12 should have the same value, likewise, C13 and C14, R11 and R12, and R13 and R14, C21 and C22, C23 and C24, R21 and R22, R23 and R24, C31 and C32, R31 and R32, R1G1 and R1G2, and R3G1 and R3G2 and so forth.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

The invention claims:

1. A system for measuring depth of anesthesia or sedation comprising
　　at least two EEG electrodes each with a lead, a circuitry for acquisition of an EEG physiological signal from the two EEG electrodes with analog front-end circuitry, a processor adapted for quantifying the filtered EEG physiological signal and a monitor for displaying a quantified, filtered EEG signal
　　the circuitry for acquisition of the EEG physiological signal comprising:
　　at least two inputs for inputting the EEG physiological signal;

at least two bootstrapped filters, each bootstrapped filter comprising a resistor, a first capacitor and a second capacitor, and a unity gain buffer, the resistor and first capacitor forming a low-pass filter and the second capacitor is driven to have substantially the same upper and lower alternating current (AC) voltage as when the EEG physiological signal enters the input, the second capacitor being driven by a common mode signal or a physiological signal potential; and at least one instrumentation amplifiers, each of the at least one instrumentation amplifier comprising at least two amplifiers;

wherein each of the two bootstrapped filters is directly connected to a common node of the at least two amplifiers of the instrumentation amplifier, the bootstrap filter being external to the instrumentation amplifier and adapted to remove common mode signal from the EEG physiological signal prior to the signal entering the instrumentation amplifier and the system is adapted to have a common mode rejection ratio of 95 or greater dB.

2. The system of claim 1, wherein the leads each comprise a shield adapted to shield the leads from outside electrical interference.

3. The system of claim 1, wherein the system further contains software or embedded algorithms that automatically identify artifacts and remove the artifacts from the physiological signal.

4. The system of claim 1, wherein the system is adapted to have a common mode rejection ratio of 100 or greater dB.

5. The system of claim 1, wherein the system has a common mode rejection ratio of 105 or greater dB.

6. A system for measuring a physiological brain signal with deep brain electrodes comprising at least two deep brain electrodes for measuring the physiological brain signal, a circuitry for acquisition of the physiological brain signal from the two deep brain electrodes with analog front-end circuitry, and an output for displaying for the physiological brain signal the circuitry for acquisition of the physiological signal with analog front-end circuitry comprising:

at least two bootstrapped filters each comprising a resistor, a first capacitor and a second capacitor, and a unity gain buffer, the resistor and first capacitor of each bootstrapped filter forming a low-pass filter and the second capacitor is driven to have substantially the same upper and lower alternating current (AC) voltage as when the EEG physiological signal is input into the system, the second capacitor being driven by a common mode signal or a physiological signal potential; and at least one instrumentation amplifier, each instrumentation amplifier comprising at least two amplifiers;

wherein the bootstrapped filters are each directly connected to a common node for each of the at least two amplifiers for each of the at least two instrumentation amplifiers, the bootstrapped filters external to each of the instrumentation amplifiers and adapted to remove common mode signal from the physiological brain signal prior to the signal entering the instrumentation amplifier, and the system is adapted to allow additional channels to be added by adding an additional bootstrapped filter and using an existing channel as a reference and the system is adapted to have a common mode rejection ratio of 95 or greater dB.

7. The system of claim 6, further comprising a processor wherein EEG signals are transmitted to the processor which is adapted to analyze the EEG signal and to calculate a quantitative EEG (QEEG) index corresponding to a subject's brain or cortical activity level.

8. The system of claim 7, wherein the system further contains software or embedded algorithms that automatically identify artifacts and remove the artifacts from the physiological signal.

9. The system of claim 6, wherein the system is adapted to have a common mode rejection ratio of 100 or greater dB.

10. The system of claim 6, wherein the system has a common mode rejection ratio of 105 or greater dB.

* * * * *